(12) United States Patent
Levisman (10) Patent No.: US 6,506,051 B2
(45) Date of Patent: Jan. 14, 2003

(54) BONE IMPLANT WITH INTERMEDIATE MEMBER AND EXPANDING ASSEMBLY

(76) Inventor: Ricardo Levisman, Aguero 1292-1° piso, 1425 Ciudad de Buenos Aires (AR)

( * ) Notice: Subject to any disclaimer, the term of this patent is extended or adjusted under 35 U.S.C. 154(b) by 0 days.

(21) Appl. No.: 09/777,101

(22) Filed: Feb. 5, 2001

(65) Prior Publication Data

US 2002/0028423 A1 Mar. 7, 2002

Related U.S. Application Data

(63) Continuation-in-part of application No. 09/654,155, filed on Sep. 1, 2000, now Pat. No. 6,350,126.

(51) Int. Cl.[7] .................................................. A61C 8/00
(52) U.S. Cl. ....................................................... 433/173
(58) Field of Search ................................ 433/172, 173, 433/174, 175, 176

(56) References Cited

U.S. PATENT DOCUMENTS

| | | | |
|---|---|---|---|
| 3,708,883 A | | 1/1973 | Flander |
| 5,004,420 A | * | 4/1991 | Soderberg ................... 433/172 |
| 5,004,421 A | | 4/1991 | Lazarof ....................... 433/173 |
| 5,015,186 A | * | 5/1991 | Detsch ........................ 433/173 |
| 5,026,285 A | * | 6/1991 | Durr et al. ................... 433/173 |
| 5,087,199 A | | 2/1992 | Lazarof ....................... 433/173 |
| 5,209,753 A | | 5/1993 | Biedermann et al. ......... 606/72 |
| 5,368,483 A | * | 11/1994 | Sutter et al. ................. 433/173 |
| 5,470,230 A | * | 11/1995 | Daftary et al. .............. 433/173 |
| 5,489,210 A | | 2/1996 | Hanosh ........................ 433/173 |
| 5,549,475 A | * | 8/1996 | Duerr et al. ................. 433/173 |
| 5,611,688 A | | 3/1997 | Hanosh ........................ 433/174 |
| 5,642,996 A | * | 7/1997 | Mochida et al. ............. 433/174 |
| 5,681,167 A | * | 10/1997 | Lazarof ........................ 433/173 |
| 5,931,674 A | | 8/1999 | Hanosh et al. .............. 433/173 |
| 6,142,782 A | | 11/2000 | Lazarof ....................... 433/174 |

* cited by examiner

Primary Examiner—Cary E. O'Connor
(74) Attorney, Agent, or Firm—Greer, Burns & Crain, LTD.

(57) ABSTRACT

A bone implant for fixing a fixing stud of a dental prosthesis into a bone, the implant being a non-expandable or an expandable implant including a tubular body and an intermediate mounting member removably mounted into the body, the intermediate member receiving the fixing stud and being capable of being removed from the body even after a long time of the implantation of the implant, thus permitting the removal of the stud from the implant in the event the stud is broken within the implant. The implant also includes, alone or in combination with the intermediate member, an expanding assembly.

31 Claims, 12 Drawing Sheets

BONE IMPLANT WITH INTERMEDIATE MEMBER AND EXPANDING ASSEMBLY

RELATED APPLICATION

This is a Continuation-In-Part of Ser. No. 09/654,155 filed Sep. 1, 2000, now U.S. Pat. No. 6,350,126.

BACKGROUND OF THE INVENTION

1. Field of the Invention

The present invention relates to a bone implant, preferably a bone implant for implanting prosthetic pieces in a bone, such as dental prosthesis in a bone, the implant comprising a fixing piece or body to be affixed in a bone and a mounting intermediate member for receiving the prosthesis piece, the mounting member being capable of being removed without traumatic effects for the patient in the event that the prosthesis or a fixing stud thereof is broken. The intermediate member can be removed even after a long time with the fixing body already integrated into the bone. Of course, the concepts of the invention are easily applied to any implant piece that must be implanted in a human being or animal bone. In addition, the invention is not only applied to expandable implants, of the type that can be initially expanded to get a retention into the bone, but also to non-expandable implants. According to the invention the implant, if of the expandable type, comprises, in combination with the intermediate member, an expanding assembly which may be operated through the intermediate member for the intermediate member for installation purposes but the intermediate member may be disengaged from the expanding assembly in order to be removed from the implant.

2. Description of the Prior Art

It is well known in medical art to provide bone implants that are useful for affixing a prosthetic piece in a bone, in replacement of any lacking natural piece or member or for joining parts of one or more bones. More, particularly, these implants are well known in the odontology wherein dental implants are used for replacing a dental piece that has been lost or extracted either in a human or animal patient. One of the problems or traumatic drawbacks of implanting a dental prosthesis in a patient is that a long time is necessary to assure to the patient that the implant is entirely or totally integrated to the bone of the patient. Generally, after the extraction or loosening of the dental piece, a fixing body of the implant is inserted and implanted into the bone and several months must pass to determine whether the fixing body has been integrated to the bone or bone fibers of the bore in the bone, this determination being necessary to continue or not with the next step of affixing the prosthetic piece into the implant. If the body has not been integrated the same must be replaced and a new waiting period begins again. This provokes anxiety and affliction in the patient who must await for months before receiving a positive diagnosis from the odontologist or the implantologist and upon a negative diagnosis the patient knows that the fixing body must be removed and that several additional months must pass. With the purpose of shortening these waiting periods, some implants, either of the expandable or non-expandable type have been developed. The expandable increased bone growth is generated. These implants are installed within the bone orifice or bore resulting from the loosened or removed dental piece or within a bore made in the bone, and the implant is radially expanded in order to get a positive initial pressure and retention. During the first weeks after the installation, it is possible to verify whether micro-mobility exists and, if the micro-mobility is detected, the implant is additionally expanded to improve the radial retention. The purpose of these additional expansions is to obtain immobility of the fixing piece that is fundamental for obtaining the integration of the piece into the bone. While these implants have been improved insofar as to the micro mobility is concerned, the same have not taken into account an important aspect of the implants, that is the need of replacing a broken prosthesis after a long elapsed time from the integration of the implant into the bone. Another aspect not taken into account by the prior art is that the expanding means used for expanding the expandable implants must be easy and safe to operate without complex and excessive friction mechanisms.

Generally, prosthetic dental pieces are affixed to a fixation stud or abutment that is installed by threading or adhesive within the fixing or mounting body that is already integrated into the bone. During the use of the prosthetic piece, if the fixing stud is broken within the fixing body that is already integrated or implanted, the broken portion of the stud that remains within the implanted body must be removed before a new prosthetic piece is re-installed. Any professional skilled in the art knows that the removal of this broken stud in the small room of the patient's mouth is very difficult if not impossible. Said broken portion is not accessible and very frequently the portion cannot be extracted, therefore the implant body must be removed from its implantation by drilling the patient's bone to release the fixing body from the bone, what is very traumatic for the patient.

The initial fixation of the implant has been treated by several professionals and disclosed in many documents like U.S. Pat. Nos. 5,004,421 and 5,087,199 to Lazarof, which disclose expandable implants having a fixing piece that is introduced and threaded into a patient's bone and has a hollow interior that is also threaded and a plurality of longitudinal cuts in the implant body. An expanding piece is arranged within the hollow interior, the piece being acceded from a top end of the fixing body by means of a tool that is introduced within the implant body to cause the expanding piece to rotate and move upwardly in order to expand the implant body to enhance the retention thereof into the bone. An upper portion of the fixation body has a threaded inner orifice for receiving a fixing stud or abutment of the dental prosthesis. While a better initial fixation is achieved, no consideration is made to the event that the prosthesis stud is broken and the prosthesis is loosened.

U.S. Pat. No. 5,489,210 discloses a dental implant having a fixation body that is introduced within the body and has a plurality of longitudinal cuts at a lower end of the body, this lower end being expanded by an expanding piece that is introduced through an upper end into the implant body and exerts a pressure against the lower end of the body to outwardly radially expand the same against the bone. Again, the initial pressure of the implant against the bone is improved but a solution to the event of a broken stud is neither disclosed nor suggested. The stud of the prosthetic piece is mounted directly within the fixing body of the implant.

U.S. Pat. No. 5,611,688 discloses an expandable dental implant also comprising a hollow tubular outer body that is affixed by expansion into the bone, the expansion being obtained by an expanding screw that is inserted into the hollow body and the initial fixation of the implant is improved. This patent does not disclose any solution to the event that the prosthesis and its fixing stud is loosened or broken. In like manner, U.S. Pat. No. 5,931,674 discloses an expandable implant very similar to Patent '688 but no means for permitting an easy removal of a broken fixing stud are provided neither the problem is addressed.

U.S. Pat. No. 3,708,883 to Flander discloses a dental implant having an elongated tubular body of the expandable type with an elongated spreader screw extending through the tubular body and a wedge-shaped spreader at a distal end of the screw, the screw being actuated by pulling means in the form of a nut which is turned to pull the spreader means beyond the nut and expand the body. Spreader threaded stem is moved upwardly and projects out from the body thus forming an obstacle for any mounting work necessary at a proximal end of the body when installing the dental prosthesis.

U.S. Pat. No. 5,209,753 to Biedermann discloses a bone screw with a shaft having threaded portions at a bottom and a top of the shaft, with a tip fixed at the bottom of the shaft to expand the bone screw when the shaft is rotated within the bone screw. First, the shaft must be rotated to be fixed to the tip and then the shaft must be unscrewed in order that the expander part be pulled into the bone screw to expand the bone screw. This is a very complex operation and an unsafe fixing and installation of the bone screw may be obtained.

U.S. Pat. No. 6,142,782 to Lazarof discloses an implant assembly comprising an elongated hollow body with an internal shoulder and a draw screw having a head captured within the hollow body and engaging the internal shoulder to form a seal with the body. While the expansion of the body is achieved by this system, no solutions are provided to the event the abutment is broken and the fixation part of the abutment remains retained within the hollow body. In addition, for installing the draw screw a screwdriver or allen wrench must be introduced into the hollow body with the inconveniencies this cause to the implantologist who must accede to the screw head without a view of same.

It would be therefore convenient to have a new expandable or non expandable implant provided with means for enhancing the initial fixation of the implant within the bone, and means for permitting the easy removal of the fixation stud of the prosthesis piece in the event the stud is broken, with a portion of the stud remaining within an implant body already integrated to the bone.

SUMMARY OF THE INVENTION

It is therefore one object of the present invention to provide a bone implant for fixing a dental prosthesis into a bone, the prosthesis being fixed into an implant body by means of a fixing stud that is fixed into the body, in the event the stud is broken and the prosthesis is loosened, the novel implant permitting the easy removal of a portion of the stud that remains within the body without the need of removing the body from the bone, the implant also comprising, alone or in combination with the intermediate member, an expanding assembly.

It is still another object of the present invention to provide a bone implant comprising a fixing tubular body for fixing in the bone, the tubular body including a distal end for being affixed within a bone bore and a proximal end for remaining accessible outside the bone and a prosthesis piece being received in the proximal end, the bone implant comprising a mounting intermediate member for mounting said prosthesis piece, the intermediate member being removably mounted within said tubular body, the intermediate member including a proximal end in communication with an inner surface for receiving a fixing stud of said prosthesis piece.

It is a further object of the present invention to provide a bone implant comprising a fixing tubular body for fixing in the bone, the tubular body including a distal end for being affixed within a bone bore and a proximal end for remaining accessible outside the bone and within the gum and for receiving a prosthesis piece, the distal end of the body including a plurality of longitudinal cuts that permit a lower portion of the body to be radially outwardly expanded by an expanding member that is received within said body, said expanding member being fixed to a distal end of a stem having a proximal end within said tubular body and a threaded outer surface, the implant also comprising a rotatable mounting intermediate member that includes a threaded inner surface within which said stem is threadably received, the mounting intermediate member including an upper end receiving the prosthesis piece.

It is still another object of the invention to provide bone implant comprising a fixing tubular body for fixing in the bone, the tubular body including a distal end for being affixed within a bone bore and a proximal end for remaining accessible outside the bone and a prosthesis piece being received in the proximal end, the bone implant comprising a mounting intermediate member for mounting said prosthesis piece, the intermediate member having an at least partially threaded outer surface for threadably connecting an at least partially threaded bore in the body, the intermediate member including an inner surface for mounting said prosthesis piece.

It is even another object of the invention to provide an expandable bone implant comprising an elongated hollow body for fixing in the bone, the tubular body including an expandable distal end for being affixed within a bone bore and a proximal end for remaining accessible outside the bone and for receiving a prosthesis piece, the bone implant comprising a bore extending along the length of the hollow body, the bore having a first proximal bore portion and a second distal bore portion, a mounting intermediate member for mounting said prosthesis piece, the intermediate member being removably mounted within the proximal bore portion of the hollow body, the intermediate member including an inner surface for mounting said prosthesis piece, and an expanding assembly comprising a screw having a proximal end and a distal end, with an expanding member threaded onto said distal end, the proximal end of the screw being removably connectable to the intermediate member in a manner that when the intermediate member is rotated in a first sense of rotation the screw is rotated in said first sense of rotation for moving the nut along the screw to expand the distal end of the body outwardly.

It is another object of the invention to provide an expandable bone implant comprising an elongated hollow body for fixing in the bone, the tubular body including an expandable distal end for being affixed within a bone bore and a proximal end for remaining accessible outside the bone and for receiving a prosthesis piece, the bone implant comprising a bore extending along the length of the hollow body, the bore having a first proximal bore portion and a second distal bore portion, a mounting intermediate member for mounting said prosthesis piece, the intermediate member being removably mounted within the proximal bore portion of the hollow body, the intermediate member including an inner surface for mounting said prosthesis piece, and an expanding assembly comprising a screw having a proximal end threaded into said intermediate member and a distal end including an expanding member, the proximal end of the screw being removably connectable to the intermediate member in a manner that when the intermediate member is rotated the screw is rotated and moved upwardly into the hollow body whereby the expanding member expands the distal end of the body outwardly, the screw including a radially extending plate forming a seal against an inner surface of the bore of the hollow body.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Now referring in detail to the drawings, FIGS. 1–5 depict an expandable bone implant according to the invention that is identified by reference number 1 and comprises a fixation or fixing tubular body 2, also called an elongated hollow body, having a distal end 3 and a proximal end 4 terminating in a coupling plate or coupling end 5 having a first cylindrical portion 6 and a second upper conical portion 7. The distal end 3 is adapted to be introduced and remain within a bone 8 and more particularly within a bore or orifice 9 that can be made artificially in the bone or corresponds to the natural orifice resulting from the extraction or loosening of a natural tooth.

When the invention is applied to an expandable implant, distal end 3 includes a plurality of longitudinal cuts 10, preferably four cuts 10. These cuts define corresponding flexible portions or deformable tongues 11 that may be slightly tapered to facilitate the initial insertion of body 2 within orifice 9. Tongues 11 will be provided with the necessary elasticity for radially outwardly expanding as it will be further explained. The outer surface of body 2 may be smooth and plain or may be provided with osseous-integration enhancing means such as being treated to enhance its adherence and obtain an improved body-bone integration. Thus, the surface may be treated and/or coated with hydroxyapatite, titanium plasma spray or acids. Depending on the bone hardness, for example, the body surface would be treated or coated, in less dense bone rough, the titanium plasma spray (TPS) and the hydroxyapatite (HA) coatings help as well by presenting maximal interfacial areas. The outer surface of body 2 may be provided with threads, projections, notches, indentations, screw machined, acid etched, machine roughened, stepped, orifices passing through the body, for enabling the bone growth entering into the body, and combinations with the above coatings. As an example, threads 12 are illustrated only at the right side in FIGS. 1, 4, 5, 6, 8–16, but, as it will be apparent to any person skilled in the art, threads 12, if provided, may extend all around the body, FIGS. 14, 17, or along a partial circumference around the body. Threads 12 may have any cross-section and configuration, preferably for obtaining a better grip between the fixation body and bone 8 to get a more stable retention.

Proximal end 4 and more particularly mounting plate 5 will remain outside bone 8 and is adapted to receive a dental prosthetic piece 13, schematically illustrated in FIGS. 1, 4, 6, 9–13, 15 and 16.

Body 2 is hollow and tubular and defines a bore 14 extending along the body and receiving an expanding member 15 having a stem 16 that is threaded along at least a part of the length thereof. While bore 14 is illustrated as being a stepped bore, the bore may be smooth, plain or straight cylindrical from one end to the opposite end. Expanding member 15 has a truncated pyramid configuration with sloped walls 17 of member 15 resting against tongues 11 of body 2 and corners 18 of the truncated pyramid are accommodated within longitudinal cuts 10, whereby any rotation of expanding member 15 is prevented by the locking or wedging effect between member 15 and cuts 10 and tongues 11. Member 15 may be, however, conical as long as the same is retained against rotation when a mounting intermediate member 19 is rotated onto screw or stem 16.

Mounting intermediate member 19 is inserted through proximal end 4, member 19 including, at its proximal end, a coupling plate 20 capable of entering in a mating relationship with the plate or coupling end 5. Plate 20 rests and abuts against end 5. Member 19 has an outer surface, preferably a smooth outer surface, adapted to be accommodated within body 2 and has a threaded interior 21 that receives threaded stem 16 of expanding member or head 15. With this assembly, by rotating intermediate member 19, either in clockwise or counterclockwise direction, a corresponding upward or downward sliding movement of member 15 and stem will be obtained because stem 16 is threadably connected to member 19 along threads 21 and member 15 is prevented from rotating within tongues 11. Upper plate 20 of member 19 is provided with a notch 22 radially extending across the plate and passing through the plate, adapted to receive the tip of a screwdriver for rotating the intermediate member. In like manner, coupling plate 5 is provided with a groove 23 extending radially across end 4 of body 2 and within end 4 along a small depth that is to be covered by prosthesis 13. By rotating intermediate member 19 notch 22 and groove 23 are capable of being placed in mating relationship in order that the tip of a screwdriver may be inserted simultaneously into both the notch and the groove. As it is described below in connection with further embodiments of the invention, plate 20 may have a nut-shape or nut projection.

Figure 1:
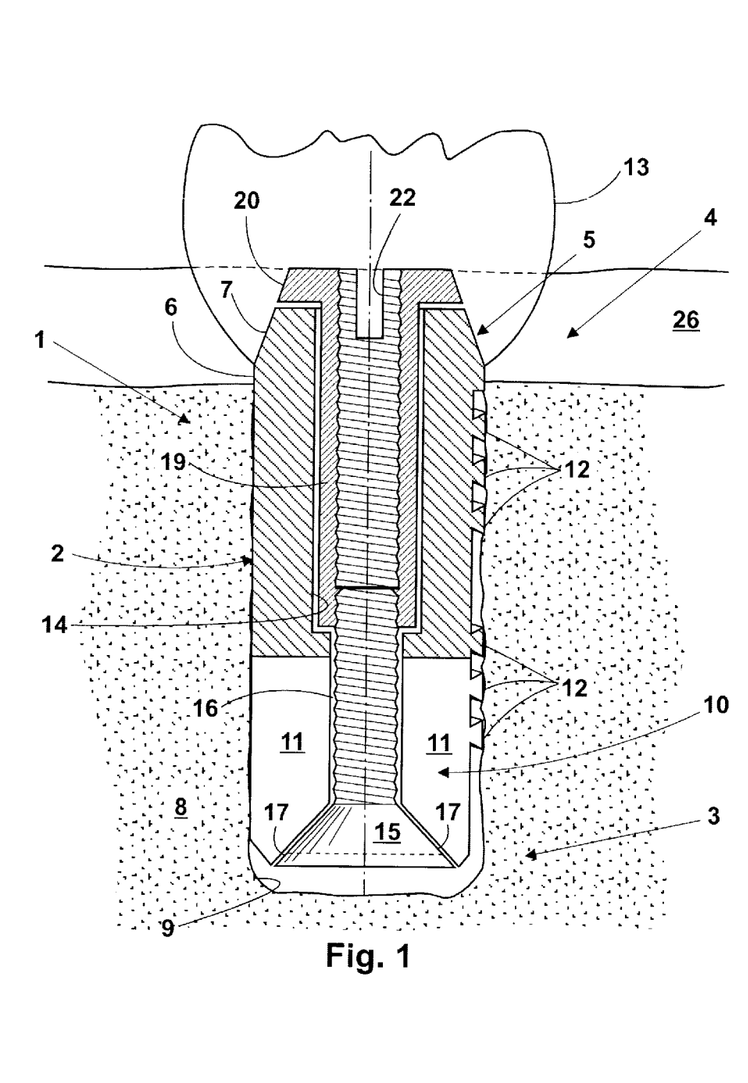
FIG. 1 shows a partially cross-sectional, elevation view of an expandable implant according to a preferred embodiment of the invention.
Figures 2, 3:
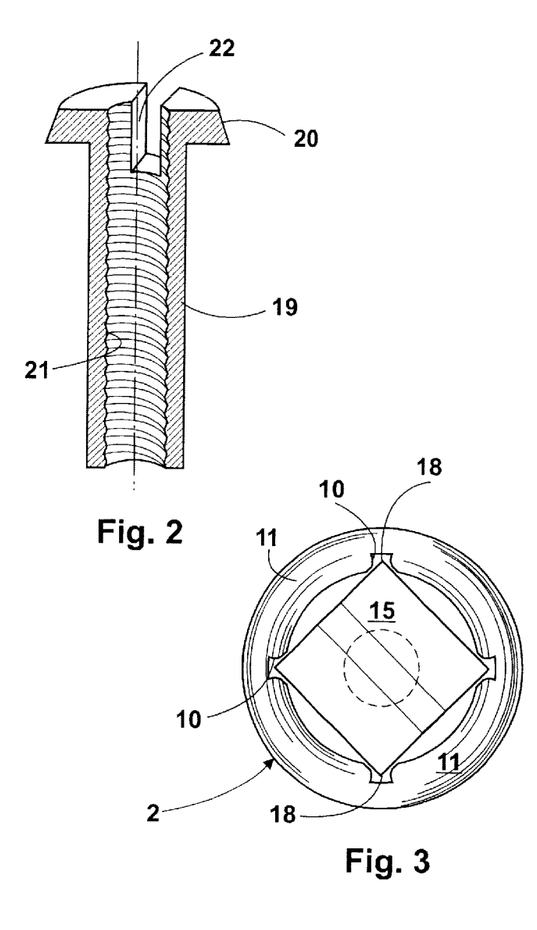
FIG. 2 shows a cross-sectional, perspective view of the mounting intermediate member of FIG. 1.
FIG. 3 shows a bottom plan view of the implant of FIG. 1.

During the operation of installing or mounting the implant within bore 9 of bone 8 the implant is arranged with its components assembled as it is shown in FIG. 1, that is, member 15 is within distal end 3 with tongues 11 in a non expanded condition. Once the implant is introduced into bore 9 as shown in FIG. 1 a tool, such as a screwdriver, is introduced into notch 22 and it is rotated until notch 22 is aligned with groove 23, see FIG. 5. With notch 22 and groove 23 in this aligned position, the tip of the screwdriver will be not only within notch 22 but also within groove 23, therefore the screwdriver may be rotated in order to rotate all the implant assembly to facilitate the introduction thereof into bore 9. If threads 12 are provided according to an embodiment of the invention, threads 12 will penetrate the bone walls like in a screw and an initial retention of the implant within the bone will be obtained. If threads 12 are not provided the rotation of implant 1 will facilitate in any case the insertion thereof into the bore.

Once the implant has been installed as shown in FIG. 1, the screwdriver is moved slightly upwardly enough to remove the screwdriver tip from groove 23 but retaining the tip into notch 22. Then, the screwdriver is rotated to cause the rotation of intermediate member 19 in such a way to cause the upward movement of stem 16 along thread 21. This upward movement will cause walls 17 of expanding member 15 to exert a radial expanding pressure against tongues 11 and to cause tongues 11 to radially expand against the wall of bore 9 as indicated by the arrows in FIG. 4. Intermediate member would be rotated until a desired retention is achieved between the outer surface of body 2, either with or without threads 12, and the bone.

Figure 4:
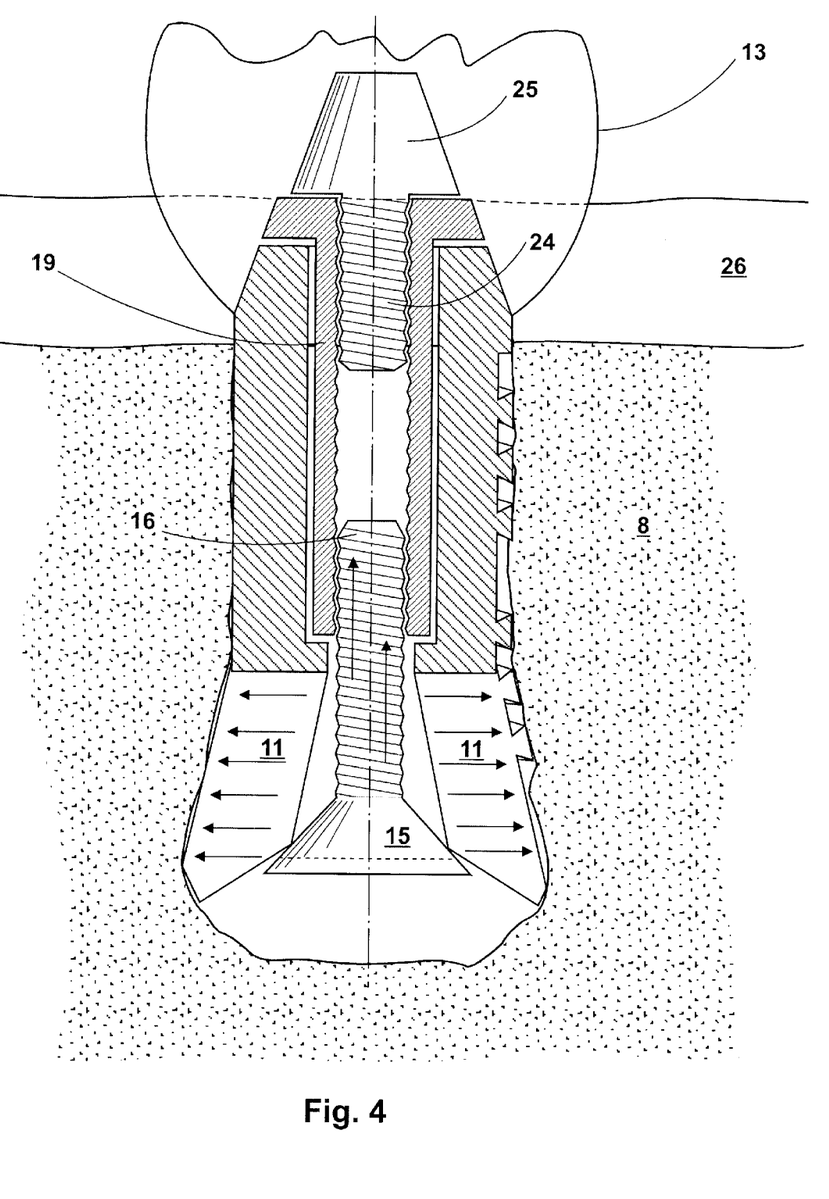
FIG. 4 shows a cross-sectional elevation view of the implant of FIG. 1 once expanded by the expanding member.
Figure 5:
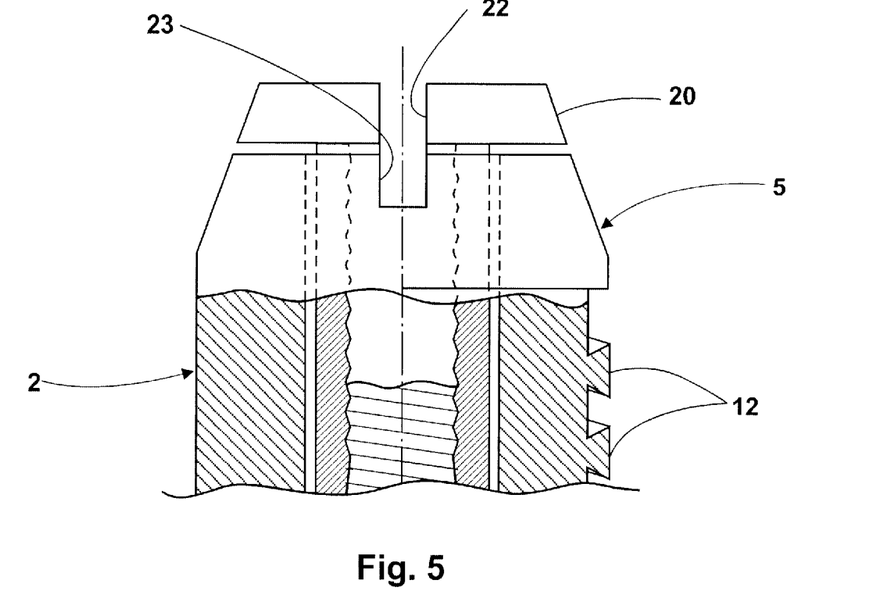
FIG. 5 shows a partial cross-sectional view of a proximal end of the implant of FIG. 1.

Prosthesis piece 13 is attached or affixed into intermediate member 19 by means of a fixing pin or stud 24 of an abutment 25, which pin or stud may be smooth or threaded, or partially smooth and partially threaded. The stud/abutment assembly may be only one integral piece or may comprise two or more parts, with a configuration either straight cylindrical or conical, as well as perpendicular or inclined. Depending on whether stud 24 is threaded, as shown in FIG. 4, or smooth (not illustrated), the stud will be threadably retained in corresponding threads 21 of member 19 or retained by adhesive or cement into at least a smooth portion of an inner surface of member 19. All this assembly is covered by prosthesis 13 that extends into gum 26 indicated by a phantom line passing through the prosthesis in FIGS. 1 and 4 for example.

In the event prosthesis 13 is loosened, for example because the stud is broken, which is a frequent accident resulting from the high forces involving the chewing, a new prosthesis must be prepared and installed in the implant. It is to be remarked that when this accident occurs, fixing body 2 is already osseous-integrated, that is integrated with the surrounding bone because of the bone growth around and into the parts of the implant.

As stated above, the removal of the portion of stud that remains broken into the implant is almost impossible to achieve and the removal of the entire implant is frequently necessary. According to the invention, if the stud is broken within intermediate member 19 and a portion of the stud remains within member 19, the removal of the stud is possible thanks to the possibility of removing member 19 by removing the same from body 2. The removal of member 19 is carried out by unscrewing the same either from stem 16, FIGS. 1, 4, 6, or from threads 31 shown in FIG. 8, by using a simple screwdriver or any other proper tool that is inserted into notch 22 only. This removal is possible even with body 2 and member 15/stem 16 are already integrated to the bone, that is completely surrounded and retained by the bone. By unscrewing, member 19 is upwardly removed in order to allow the implantologist to repair the prosthesis by easily removing the broken portion of the stud from member 19 or to install a new intermediate member containing a new prosthesis and stud. This is a remarkable improvement as compared to the prior art because the traumatic removal of the fixing body already integrated to the bone is avoided in benefit of the patient's comfort and the implantologist's practice.

While the concepts of the invention have been illustrated and disclosed in relation to an implant of the expandable type, as illustrated in FIGS. 1–5, it must be understood that the invention is likewise applicable to non-expandable implants such as illustrated in FIGS. 6, 7, 10 and 11.

Figure 6:
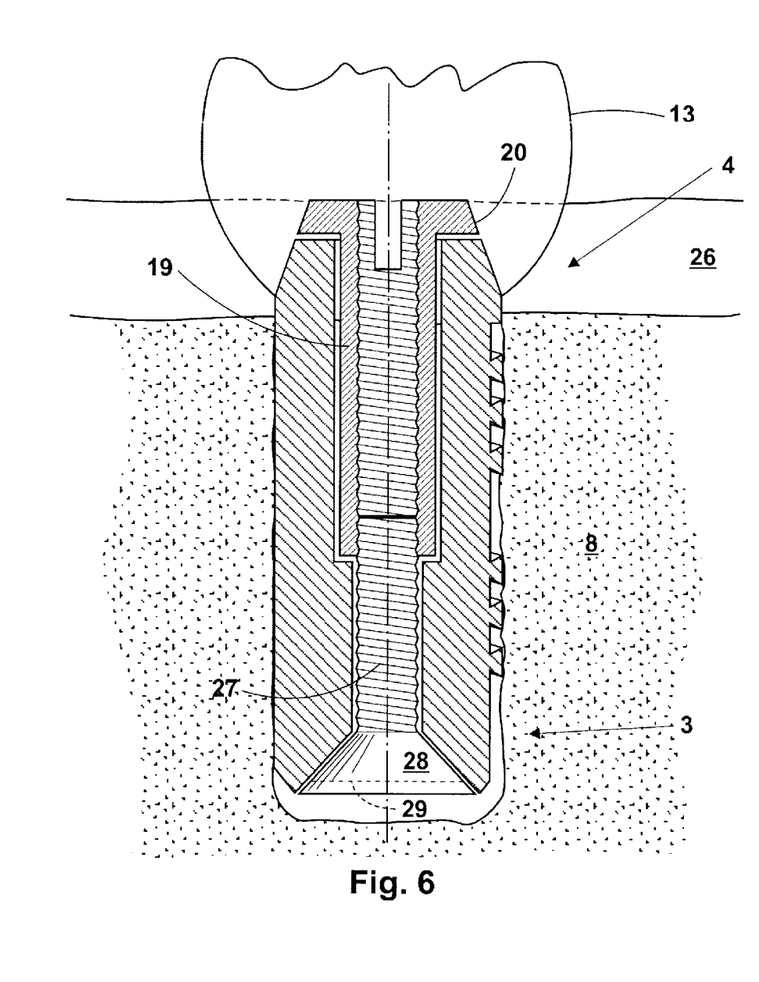
FIG. 6 shows a partial cross-sectional, elevation view of a non-expandable implant according to another preferred embodiment of the invention.
Figure 7:
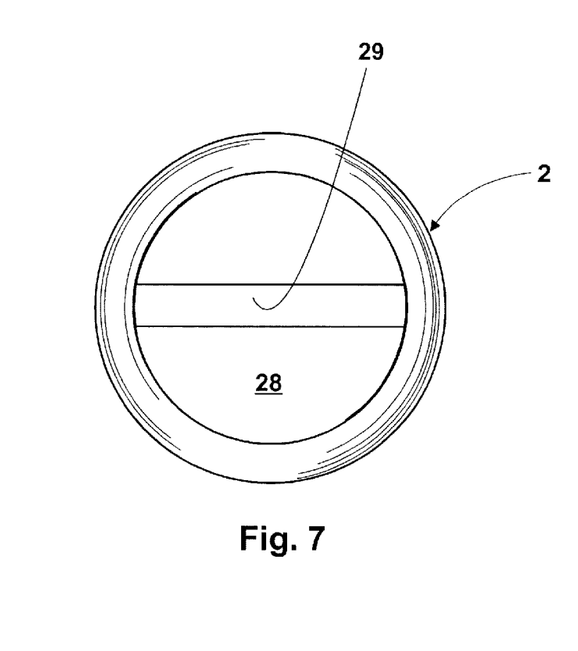
FIG. 7 shows a bottom plan view of the implant of FIG. 6.

As shown in FIGS. 6, 7, the equivalent components of the invention are identified in these Figures with the same reference numbers of FIGS. 1–5. Thus, intermediate member 19 may be like any of the ones illustrated in FIGS. 1–5, but fixation body 2 of FIGS. 6, 7, differing from body 2 of FIGS. 1–5, has a distal end 3 without cuts 10, that is the body is entirely cylindrical therefore, without expansion capability. Instead of an expanding member 15, a simple screw 27 is provided, the screw having a conventional head 28 provided with an actuating groove 29 for receiving the tip of a screwdriver to rotate the screw and screw the same into intermediate member 19 upon assembling the implant before installing the same into bore 9. The purpose of screw 27 is to retain intermediate member 19 within fixation body 2. After the osseous-integration of body 2 has been completed, if the prosthesis stud (not illustrated in FIG. 6) is broken, intermediate member 19 may be easily removed by unscrewing the same by means of a screwdriver, for example.

Figure 8:
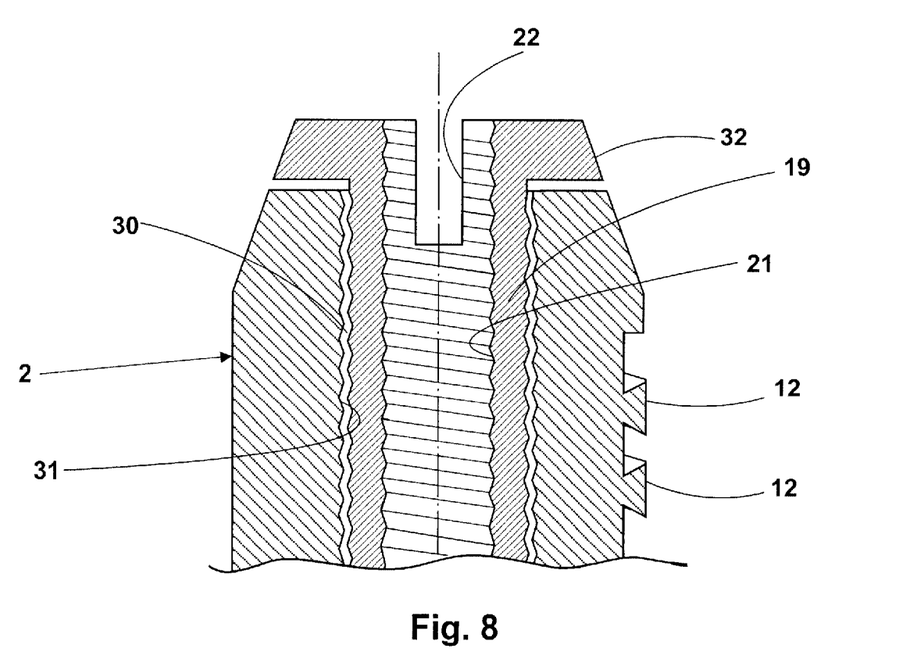
FIG. 8 shows a partial cross-sectional view of a proximal end of the implant according to another embodiment of the invention.

According to another alternative embodiment of the invention, shown in FIG. 8, the outer surface of intermediate member 19 has threads 30, along a total or partial length of the member, and bore 14 inside body 2 is provided with threads 31 extending along the entire or partial length of the bore, whereby intermediate member 19 may be threadably and removably mounted within body 2 without the need of any additional screw 27 like the one of FIG. 6. Inner threads 21 and threads 30, 31 and 12 preferably have the same helical sense to prevent member 19 from loosening from body 2, or body from loosening from bore 9, when stud 24 is being screwed into intermediate member 19. Member 19 may define, at its proximal end, a head or plate 32 provided with a groove 22 for receiving a screwdriver, or the head or plate may have a polygonal configuration, quadrangular, hexagonal, for connecting a wrench, for example.

Figure 9:
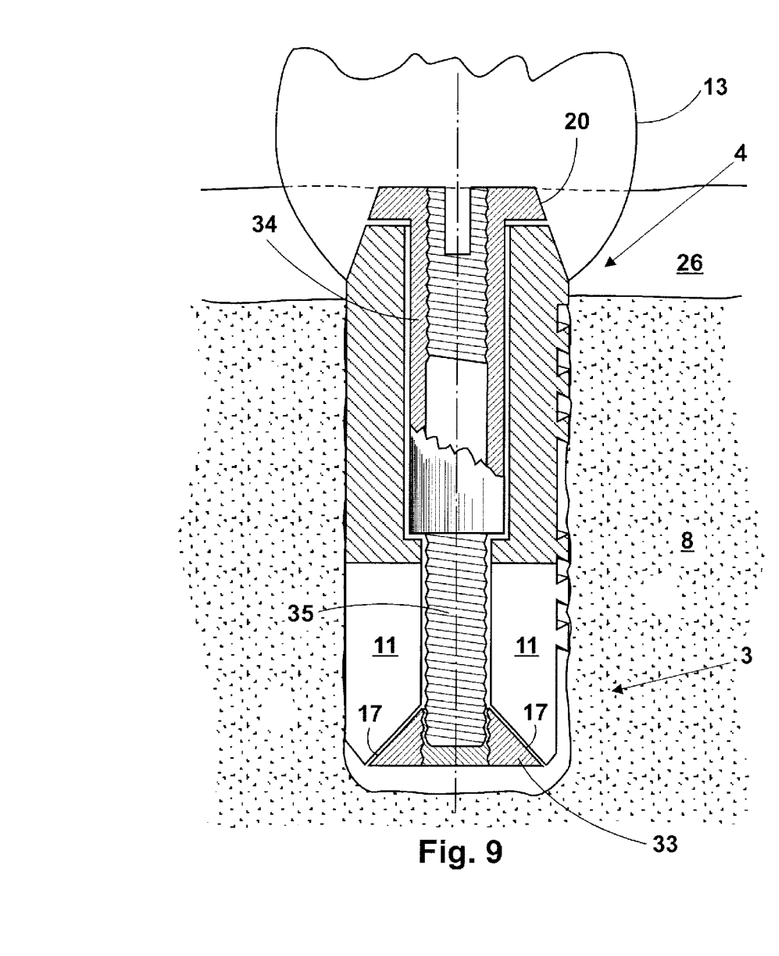
FIG. 9 shows a partial cross-sectional, elevation view of an expandable implant according to another preferred embodiment of the invention.

FIG. 9 shows an expandable bone implant according to another alternative embodiment of the invention wherein the expanding member 15 of FIG. 1 consists of an expanding nut 33 also having sloped walls 17, and threaded stem 16 of FIG. 1 is replaced by stem 35 not joined to the expanding member but to the intermediate member now indicated with reference number 34. Similar to the assembly of FIG. 1, by rotating intermediate member 34, either in clockwise or counterclockwise direction, a corresponding upward or downward sliding movement of member 33 along stem 35 will be obtained because stem 35 is threadably connected to nut 33 which is prevented from rotating within tongues 11. Nut 33 may be pyramidal or conical, or a combination or both shapes, but is always recommended to be prevented from rotation. Stem 35 may be an integral part of intermediate member 34 or may be joined by any proper manner like welding, etc.

Figure 10:
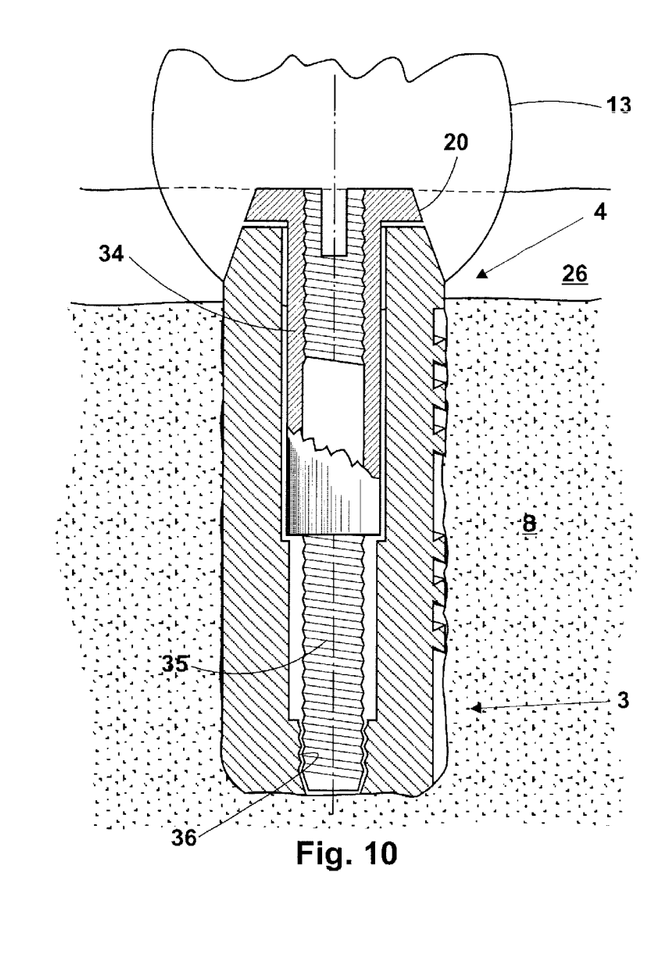
FIG. 10 shows a partial cross-sectional, elevation view of a non-expandable implant according to another preferred embodiment of the invention.

According to another alternative embodiment FIG. 10 shows a non-expandable implant similar to the implant of FIG. 6, wherein a threaded stem 35/intermediate member 34 like the assembly shown in FIG. 9 has been used to replace screw 27/head 28. Since this is a non-expandable implant no expanding member is provided and, instead, body 2 is provided with a threaded bottom bore 36 at bottom end 3. Like the above embodiments, member 34 has an inner surface that may be entirely or partially threaded as shown in FIGS. 9, 10, and stud 24 may be, accordingly, a threaded or a smooth stud or a partial threaded and a partial smooth stud.

As it is very clear to any expert in the art, if the abutment or stud of a prosthesis is broken with a portion of the stud remaining broken within intermediate member 19, 34, the stud portion, together with the intermediate member, may be easily removed from the fixation body for repairing the prosthesis and installing a new one. It may occur, however, that in some of the above disclosed embodiments of the invention, the intermediate member is somewhat affected by the osseous-integration when the member has to be removed.

According to the above remarked difficulty, while the expanding members like the stems or screws and nuts snugly fit one into the others and into the tubular body, the bone may growth through cuts 10 and into bore 14 of body of FIGS. 1, 4 and 9 and reach the intermediate member 19, 34 and, while in a minor extent, adheres to the intermediate member and may prevent the same from being easily rotated, by using a slight force, in the event the intermediate member must be removed from the tubular body.

Figure 11:
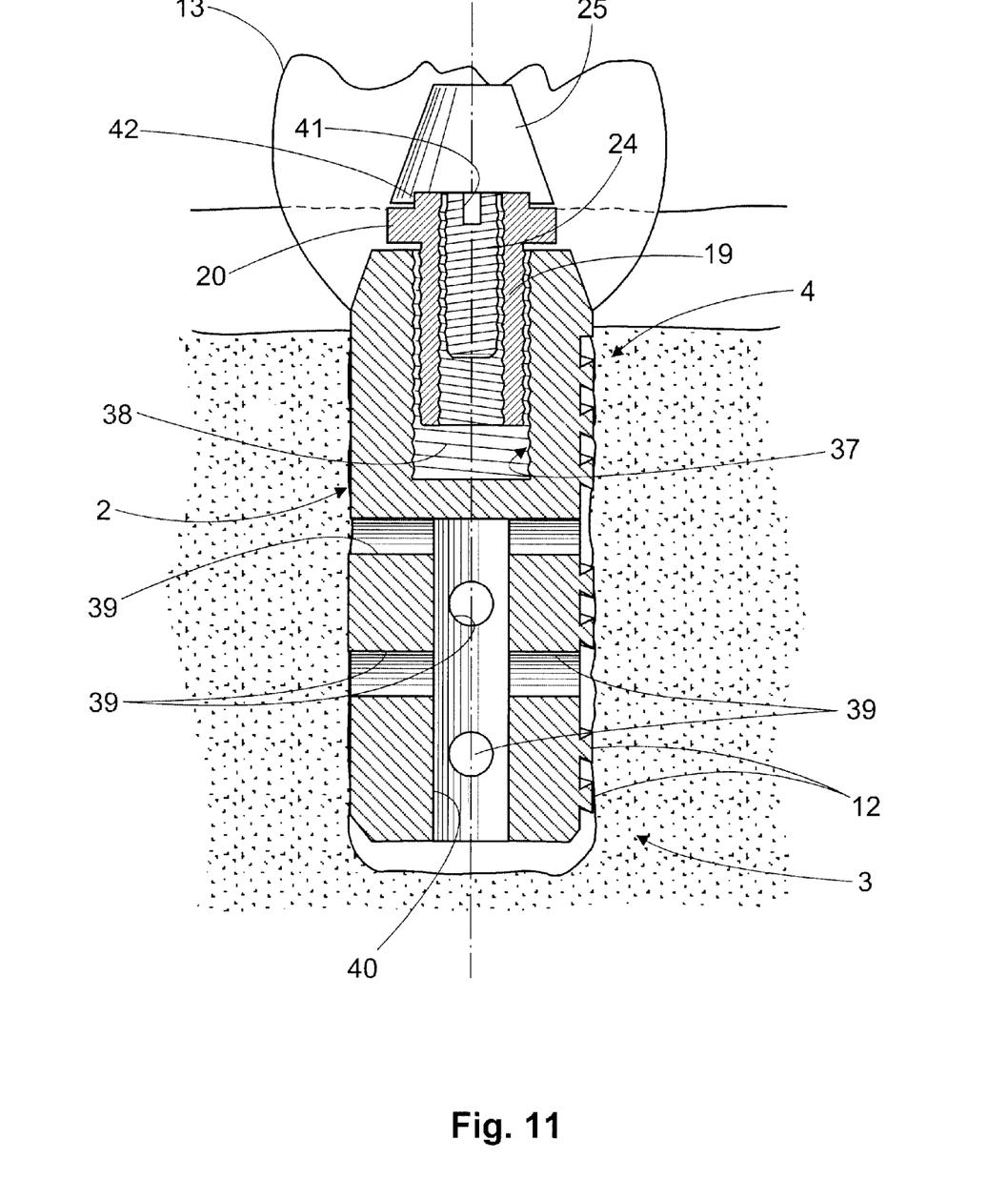
FIG. 11 shows a partial cross-sectional elevation view of a non-expandable implant according to another preferred embodiment of the invention.

According to another embodiment of the invention shown in FIG. 11, the intermediate member is prevented from entering into contact with the growing bone. The equivalent components of the invention are identified in these Figures with the same reference numbers of above described Figures. Thus, intermediate member 19 may be like the ones illustrated in FIGS. 1–8, having a shorter length and isolated from the bone. Fixation tubular body 2, however is provided with a bore 37 that is internally threaded 38 and is blind, that is it does not run all along the length of the body and does not pass entirely through the body from proximal end 4 to distal end 3. Distal end 3 may be provided with osseous-integration enhancing means comprising orifices or threads 12 illustrated only at one side of the body for clarity purposes. It may be seen that any bone growth may enter orifices 39 and a bottom bore portion 40 of the body without acceding to upper bore 37.

Plate 20 of the intermediate member may be provided with an actuating groove 41 for receiving the tip of a screwdriver to rotate the intermediate member and screw the same into bore 37, or plate 20 may have a nut-shape or a nut projection 42 for using a wrench. Both, a groove 41 and a nut configuration may be combined. Proximal end 4 of the hollow body may also be provided with an outer surface having a nut design. In this and in all of the embodiments, end portion 6 is preferably polished in order to prevent the adherence of bacteria plaques. After the osseous-integration of body 2 has been completed, if prosthesis stud 24 (only shown in FIG. 11 for clarity purposes, but valid also for the other Figures) is broken, intermediate member 19 may be easily removed by unscrewing the same by means of a screwdriver, a wrench, etc.

Figure 12:
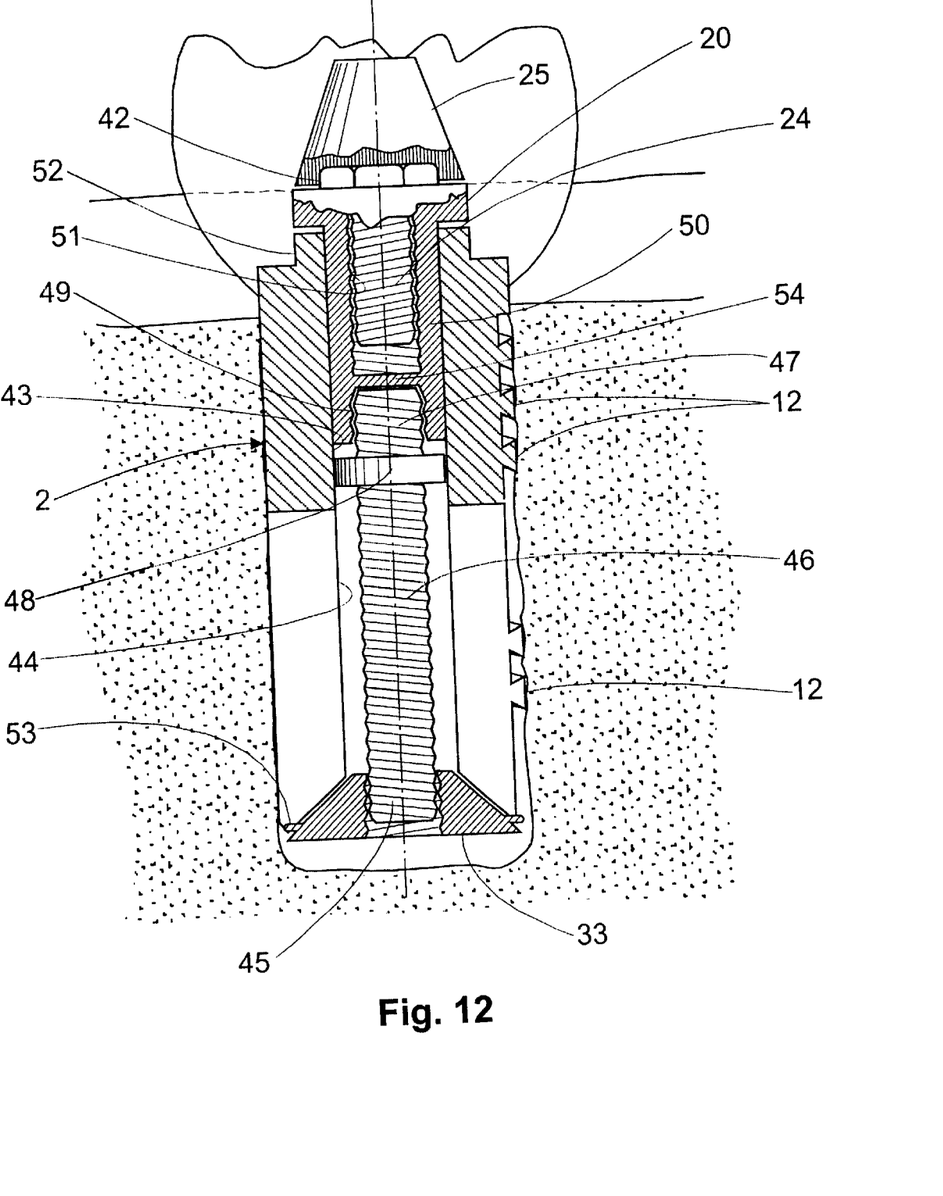
FIG. 12 shows a partial cross-sectional elevation view of an expandable implant according to a further embodiment of the invention.
Figure 13:
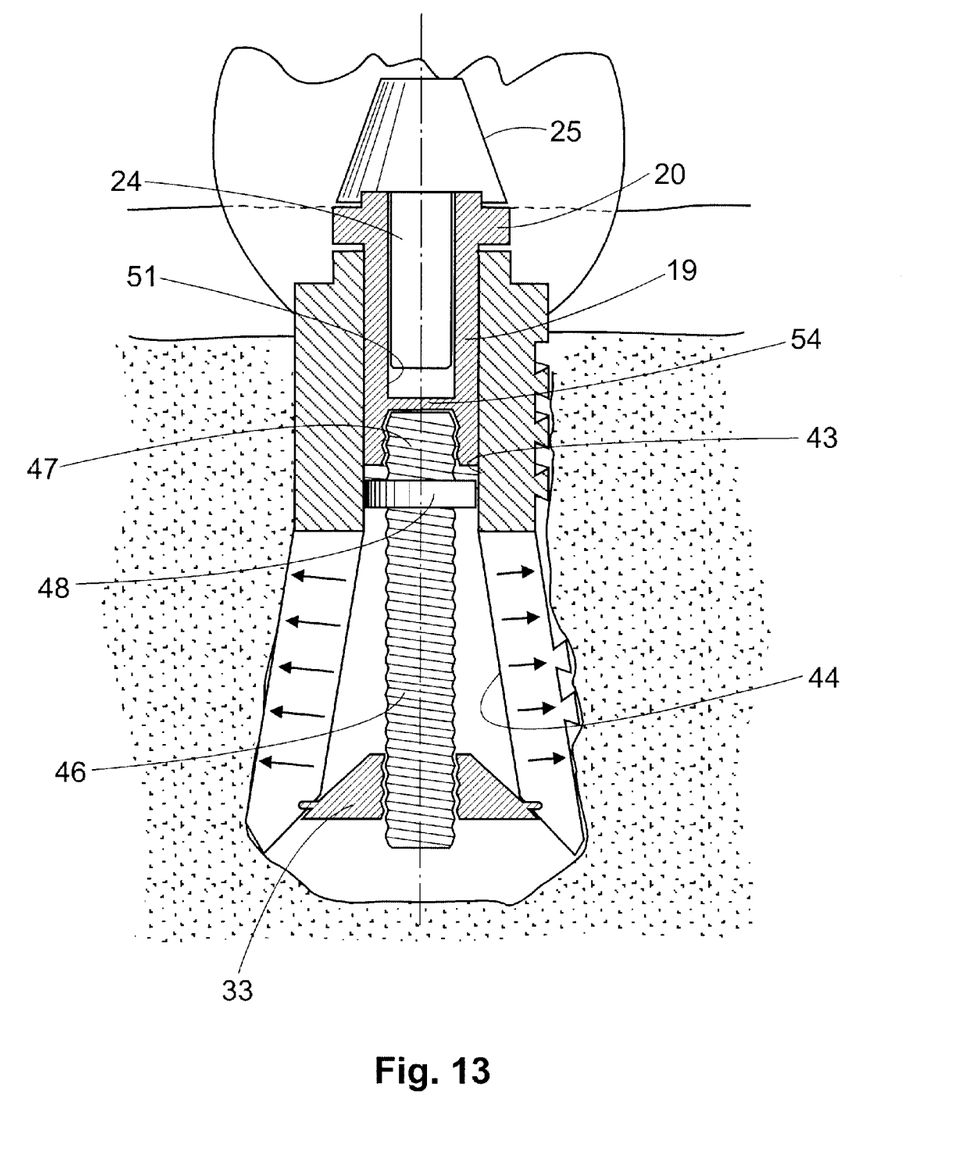
FIG. 13 shows a partial cross-sectional elevation view of the implant of FIG. 12 once expanded by the expanding assembly.

According to even another embodiment of the invention, the shorter intermediate member 19 of FIG. 11 may also be employed in an expandable implant and combined with expanding means. Thus, body 2, FIG. 12, includes longitudinal bore 14 extending along the length of the hollow body, bore 14 being smooth, without threads, and having a first proximal bore portion 43 and a second distal bore portion 44. An expanding assembly for outwardly expanding the distal portion of the body is also provided, the expanding assembly comprising a screw 46 having a proximal end 47 and a distal end 45 with an expanding member which may be like nut 33 of the other embodiments. End 47 is capable of being housed within a cavity 49 at a distal end of an intermediate member 50 and cavity 49 is provided with means for removably retaining end 47, these means being preferably a thread. Therefore, member 50 differs from member 19 of the other embodiments in that distal cavity 49 is provided which is isolated from the proximal inner portion of the member, wherein stud 24 of abutment 25 is received, by an inner wall 54. This proximal inner portion 51 may be threaded, as it is illustrated in FIG. 12, or may be smooth as shown in FIG. 13, in order to receive the stud which must be also stud and may be fixed by any appropriate adhesive or cement. In fact, wall 54 is appropriate for use with prosthesis and abutments having a stud that is adhered into intermediate member 50 by means of an adhesive, therefore with the inner surface of the intermediate member being preferably smooth and with the adhesive prevented from entering into contact with screw end 47. As an example, stud 24 and inner surface 51 are shown in FIG. 13 as being both smooth, that is without threads, apt to receive an adhesive like a cement.

Like in the previous embodiments, member 50 may be provided with a nut-shaped projection 42 for using a wrench or a notch 41 (see FIG. 11) for using a screwdriver, in order to screw member 19 into bore portion 43 or to rotate member 50 in order to expand the tubular body through nut member 33. Nut projection 42 is useful for mounting abutment 25. In like manner, the proximal portion 4 of the hollow body may be provided with a nut configuration at 52 in order to rotate and introduce the body into the bone by means of a tool.

Screw 46 is also provided with a disc-like plate 48 or radially extending plate forming a seal against an inner surface of proximal bore portion 43 of the hollow body. Plate 48 is fixed to screw 46 and prevents the bone growing from entering into contact with the intermediate member, whereby intermediate member may be free and can be removed at any time by rotating the same in a sense of rotation opposite to a first sense of rotation through which the member was rotated to be coupled to end 47, thus, member 50 may be unscrewed from screw 46 without any obstacle. Preferably, all the threads in the components are in the same sense of rotation.

Nut 33 is threaded onto said distal end of the screw for moving along the screw to expand the body outwardly. When intermediate member 50 is rotated in a first sense of rotation through its end 20 or 42 screw 46 is also rotated in the same sense of rotation. Nut 33 is retained against rotation in said distal end of the tubular body but permitted to slide along the screw when the screw is rotated, as it is shown in FIG. 13. Screw 46 is preferably rotated in the same direction that the body is rotated when introduced into the bone. Thus, nut may be pyramidal or conical or have any other convenient shape. If pyramidal, the expanding nut has a truncate pyramid shape with its vertexes in said longitudinal cuts of the tubular body. Alternatively, nut 33 may be provided with one or more projections of which only one indicated with 53 is shown in FIGS. 12–14, with projection 53 being located within a cut 10, between two adjacent tongues 11.

Figure 14:
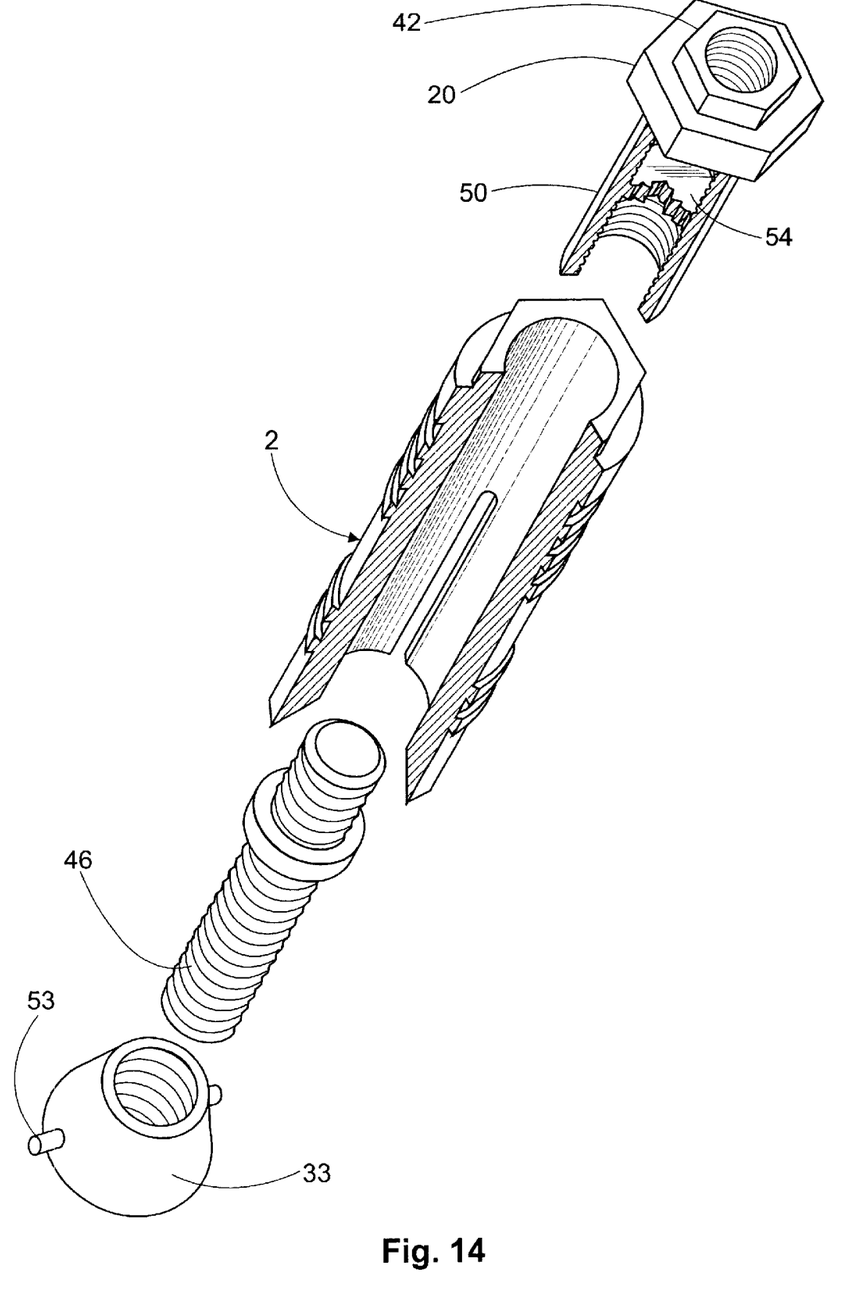
FIG. 14 shows an exploded partial cross-sectional diagrammatical view of the implant of FIG. 12.
Figure 15:
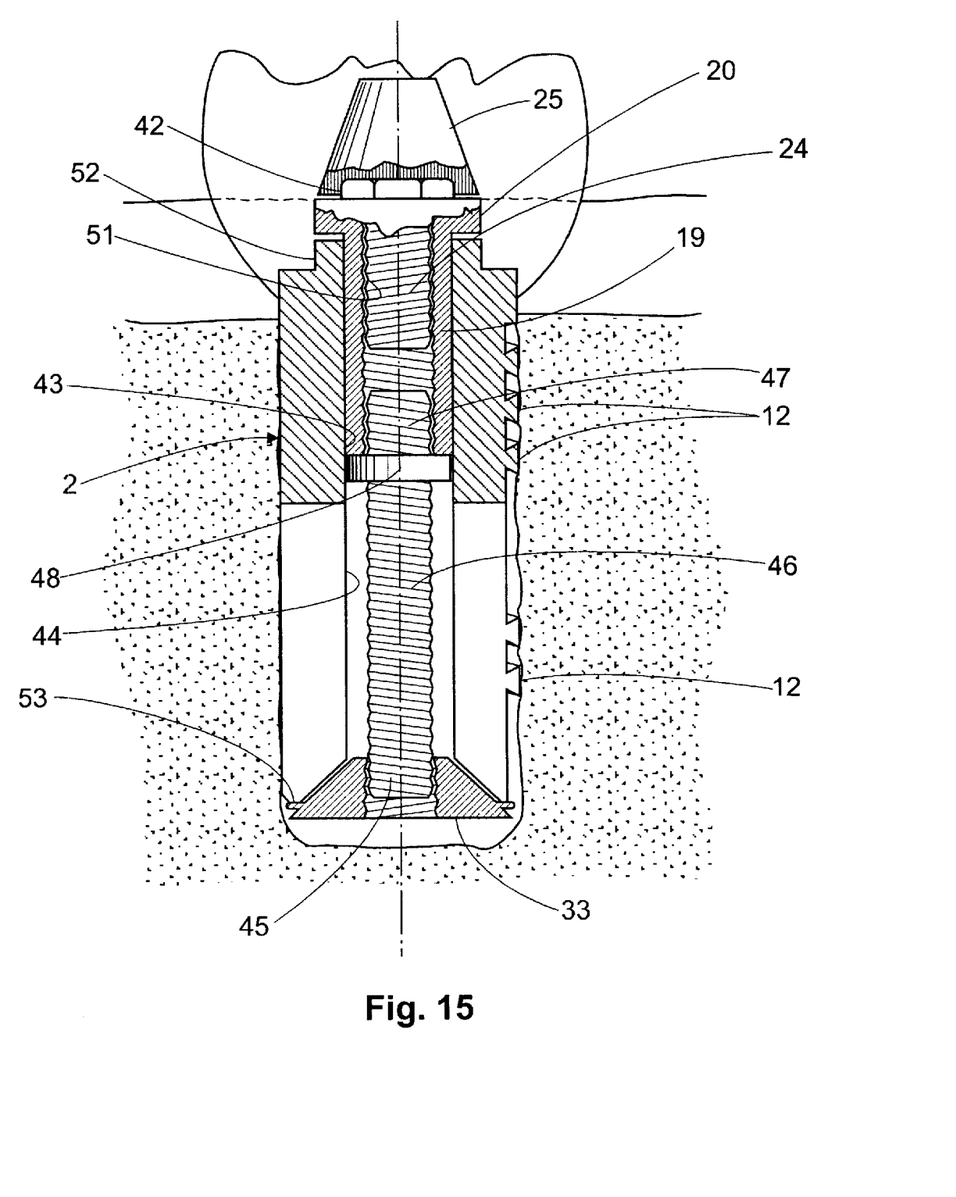
FIG. 15 shows a partial cross-sectional elevation view of an expandable implant according to a further embodiment of the invention.
Figure 16:
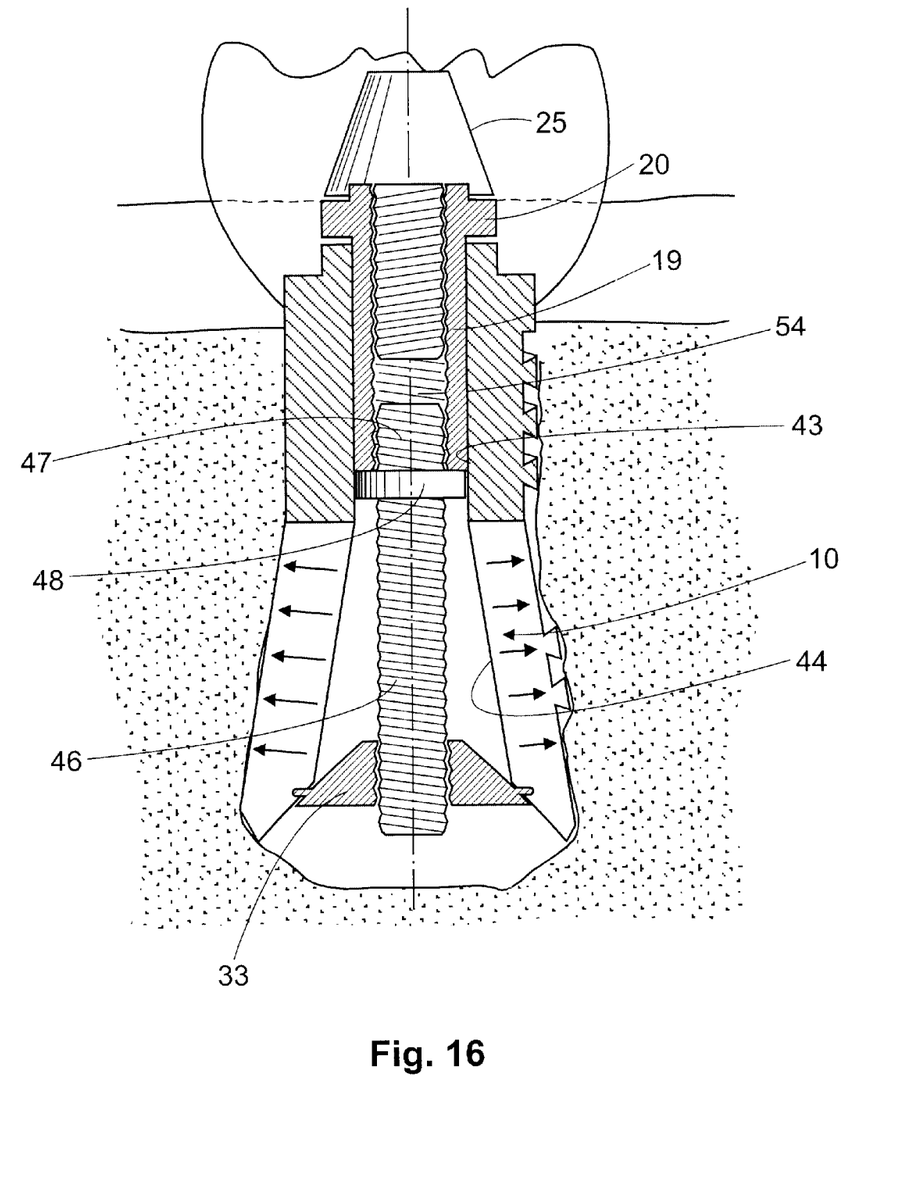
FIG. 16 shows a partial cross-sectional elevation view of the implant of FIG. 15 once expanded by the expanding assembly.
Figure 17:
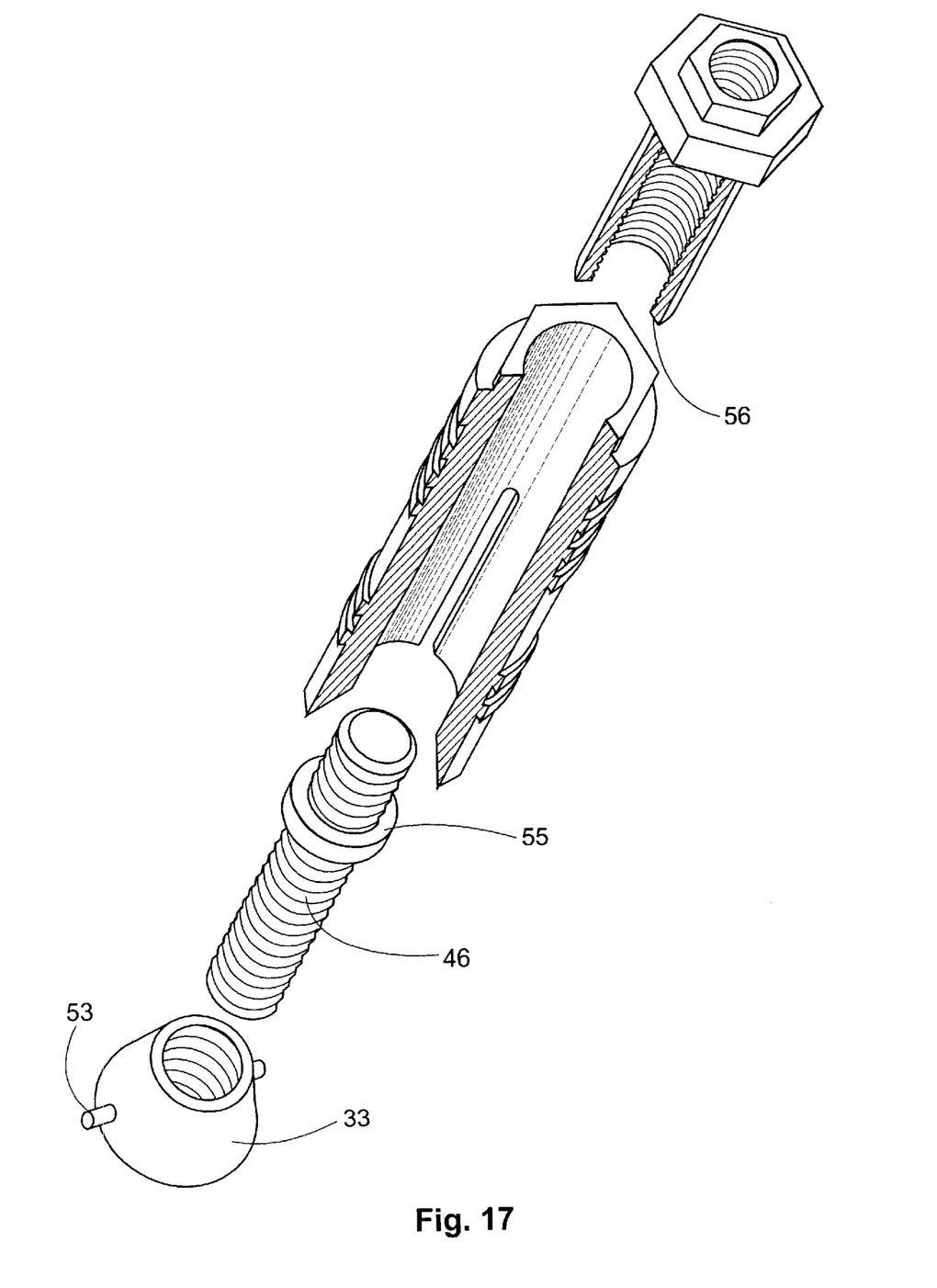
FIG. 17 shows an exploded partial cross-sectional diagrammatical view of the implant of FIG. 15.

Even according to another embodiment of the invention, shown in FIGS. 15–17, the implant is basically like the one of FIGS. 12–14 but the intermediate member 50 is replaced by intermediate member 19, which is like the intermediate member shown in FIGS. 1–8, with a length as desired to permit a removable connection between the distal portion of the intermediate member with end 47 of screw 46. With intermediate member 19 connected to end 47 of screw 46, as shown in FIGS. 15, 16, an upper sealing surface 55 of sealing plate 48, see FIG. 17, abuts against a bottom edge 56 of the intermediate member, whereby any bone growing through cuts 10 cannot reach the intermediate member when screw 46 and member 19 are connected and the body expanded as shown in FIG. 16.

In all of the above embodiments, the abutment and stud may be made of die cast metal other than Titanium, straight or inclined at about 15°–25° and since they are not in contact with the saliva no galvanic currents are generated between the stud and the body which is generally made of titanium.

While preferred embodiments of the present invention have been illustrated and described, it will be obvious to those skilled in the art that various changes and modifications may be made therein without departing from the scope of the invention as defined in the appended claims.

I claim:

1. A bone implant comprising:
   a fixing tubular body for fixing in a bone, the tubular body including a distal end for being affixed within a bone bore and a proximal end for remaining accessible outside the bone;
   a prosthesis piece being received in the proximal end,
   a mounting intermediate member for mounting said prosthesis piece, the intermediate member having an at least partially threaded outer surface for threadably connecting an at least partially threaded bore in the body,
   the intermediate member including an inner surface for mounting said prosthesis piece and a proximal end;
   wherein said proximal end of the fixing tubular body defines a coupling end and said proximal end of the intermediate member has a corresponding coupling plate abutted against the coupling end; and
   wherein the plate of the intermediate member includes one of a nut-shape projection or head for threading the intermediate member into the tubular body and a notched head for screwing the mounting member into the tubular body by means of a screwdriver, for inserting the tubular body into the bone.

2. A bone implant comprising a fixing tubular body for fixing in the bone, the tubular body including a distal end for being affixed within a bone bore and a proximal end for remaining accessible outside the bone and a prosthesis piece being received in the proximal end, the bone implant comprising:
   a mounting intermediate member for mounting said prosthesis piece, the intermediate member having an at least partially threaded outer surface whereby the intermediate member is threadably removably mounted into an at least partially threaded blind bore in the proximal end of the tubular body, the intermediate member including an inner surface for mounting said prosthesis piece and a proximal end directly abutting said proximal end of the tubular body, the proximal end of the intermediate member including means for connecting a tool for easily removing the intermediate member from the blind bore in the body; and said proximal end of the fixing tubular body defines a coupling end and said proximal end of the intermediate member has a corresponding coupling plate abutted against the coupling end.

3. The bone implant of claim 2, wherein the inner surface of the intermediate member receives a fixing stud of said prosthesis piece.

4. The bone implant of claim 3, wherein the inner surface of the intermediate member is smooth and receives said fixing stud of the prosthesis piece, the stud being smooth and is fixed within the intermediate member by adhesive cement.

5. The bone implant of claim 3, wherein the inner surface of the intermediate member is threaded and the fixing stud of said prosthesis piece is threadably mounted in said inner surface of the intermediate member.

6. The bone implant of claim 3, wherein the inner surface of the intermediate member and the stud are partially threaded and partially smooth.

7. The bone implant of claim 2, wherein the means for connecting a tool is provided in the plate of the intermediate mounting member and includes a nut-shape projection or head for threading the mounting member into the tubular body and for inserting the tubular body into the bone.

8. The bone implant of claim 2, wherein the means for connecting a tool is provided in the plate of the intermediate mounting member and includes a notched head for screwing the mounting member into the tubular body by means of a screwdriver and for inserting the tubular body into the bone.

9. The bone implant of claim 8, wherein said proximal end of the fixing tubular body defines a nut configuration and has a diameter larger than the diameter of the notched head of the intermediate member.

10. The bone implant of claim 2, wherein the tubular body has an outer surface provided with threads.

11. The bone implant of claim 2, wherein said proximal end of said intermediate member has a polygonal configuration.

12. The bone implant of claim 2, wherein a portion of the tubular body close to the distal end of the body is provided with an osseous-integration enhancing means.

13. The bone implant of claim 12, wherein the osseous-integration enhancing means comprises projections.

14. The bone implant of claim 12, wherein the osseous-integration enhancing means comprises orifices passing through the body for enabling the bone growth entering into the body.

15. An expandable bone implant comprising an elongated hollow body for fixing in the bone, the elongated hollow body including an expandable distal end for being affixed within a bone bore and a proximal end for remaining accessible outside the bone and for receiving a prosthesis piece, the bone implant comprising:
   a bore extending along the length of the hollow body, the bore having a first proximal bore portion and a second distal bore portion,
   a mounting intermediate member for mounting said prosthesis piece, the intermediate member being removably mounted within the proximal bore portion of the hollow body, the intermediate member including an inner surface for mounting said prosthesis piece, and an expanding assembly comprising a screw having a proximal end and a distal end, with an expanding member threaded onto said distal end, the proximal end of the screw being removably connectable to the intermediate member in a manner that when the intermediate member is rotated in a first sense of rotation the screw is rotated in said first sense of rotation for moving the expanding member along the screw to expand the distal end of the body outwardly.

16. The bone implant of claim 15, wherein the distal end of the tubular body includes a plurality of longitudinal cuts defining an expandable portion that is capable of being radially outwardly expanded by the expanding assembly, wherein the expanding member comprises an expanding nut threadably mounted onto the screw, the nut being retained against rotation in said distal end of the tubular body but permitted to slide along the screw.

17. The bone implant of claim 16, wherein the expanding nut has a truncate pyramid shape with its vertexes in said longitudinal cuts of the tubular body.

18. The bone implant of claim 16, wherein the expanding nut has a cone shape and includes projections extending within said longitudinal cuts of the tubular body.

19. The bone implant of claim 15, wherein the proximal end of the body has an outer nut-shape for rotating the body by means of a wrench and threading the body into the bone bore.

20. The bone implant of claim 15, wherein the intermediate member includes a proximal end with an outer nut configuration for mounting a tool for rotating the intermediate member.

21. The bone implant of claim 15, wherein the intermediate member includes a distal end with a cavity for receiving said proximal end of the screw, the cavity including means for removably connecting the intermediate member with the screw.

22. The bone implant of claim 21, wherein the means for removably connecting the intermediate member with the screw comprises a thread within the cavity.

23. The bone implant of claim 21, wherein the intermediate member includes an inner wall isolating said cavity from an inner surface of the intermediate member that receives said fixing stud of the prosthesis piece.

24. The bone implant of claim 15, wherein the screw includes a radially extending plate forming a seal against an inner surface of the bore of the hollow body.

25. The bone implant of claim 24, wherein the radially extending plate abuts against a distal end of the intermediate member when the screw is removably coupled to the intermediate member.

26. The bone implant of claim 15, wherein the inner surface of the intermediate member receives a fixing stud of said prosthesis piece.

27. The bone implant of claim 26, wherein the inner surface of the intermediate member is smooth and receives said fixing stud of the prosthesis piece, the stud being smooth and is fixed within the intermediate member by adhesive cement.

28. The bone implant of claim 26 wherein the inner surface of the intermediate member is threaded and the fixing stud of said prosthesis piece is threadably mounted in said inner surface of the intermediate member.

29. The bone implant of claim 26, wherein the inner surface of the intermediate member and the stud are partially threaded and partially smooth.

30. The bone implant of claim 15, wherein the tubular body has an outer surface provided with threads.

31. The bone implant of claim 15, wherein a portion of the tubular body close to the distal end of the body is provided with a plurality osseous-integration enhancing means.

* * * * *